United States Patent
Tsuboi et al.

(10) Patent No.: US 6,542,238 B1
(45) Date of Patent: Apr. 1, 2003

(54) ELECTRONIC COMPONENT MOUNTING APPARATUS

(75) Inventors: Yasutaka Tsuboi, Osaka (JP); Kazuyuki Nakano, Yamanashi (JP); Shozo Fukuda, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/622,825

(22) PCT Filed: Feb. 26, 1999

(86) PCT No.: PCT/JP99/00904
§ 371 (c)(1),
(2), (4) Date: Oct. 12, 2000

(87) PCT Pub. No.: WO99/44409
PCT Pub. Date: Sep. 2, 1999

(30) Foreign Application Priority Data

Feb. 27, 1998 (JP) ............................................ 10-047865
Nov. 25, 1998 (JP) ............................................ 10-333914

(51) Int. Cl.$^7$ .............................................. G01B 11/00
(52) U.S. Cl. .................................................... 356/401
(58) Field of Search .......................... 250/216; 396/272; 356/400, 401

(56) References Cited

U.S. PATENT DOCUMENTS

| 4,367,463 A | * | 1/1983 | Suzuki et al. ............... 396/296 |
| 4,972,307 A | * | 11/1990 | Takatsuji et al. ............ 362/299 |
| 5,130,531 A | | 7/1992 | Ito et al. |
| 5,162,844 A | * | 11/1992 | Ueda .............................. 355/67 |
| 5,710,671 A | | 1/1998 | Bichlmaier |
| 5,784,656 A | * | 7/1998 | Utagawa ...................... 396/272 |
| 6,386,669 B1 | * | 5/2002 | Scofield et al. ............. 347/105 |
| 6,400,099 B1 | * | 6/2002 | Walker ......................... 359/184 |

FOREIGN PATENT DOCUMENTS

| JP | 4-122840 | 4/1992 |
| JP | 9-116297 | 5/1997 |
| JP | 10-145100 | 5/1998 |

\* cited by examiner

*Primary Examiner*—John R. Lee
*Assistant Examiner*—Johnnie L Smith, II
(74) *Attorney, Agent, or Firm*—Wenderoth, Lind & Ponack, L.L.P.

(57) ABSTRACT

An electronic component mounting apparatus (1) includes a device for illuminating a mark (9) on a printed circuit board (14) for recognition. The illumination device (10) includes a light path adjustable member (5). This light path adjustable member (5) is disposed between an illumination source unit (2) and the object (9) to be illuminated. At least one of the light incidence side and the emission side of the light path adjustable member (5) is divided into a plurality of subareas (6), (7), (8), each having a different index of refraction. Each of the subareas (6), (7), (8) emits light at a respective different index of refraction. The emitted light can be collected on a specific area containing the object (9), and appropriate illumination light can thus be emitted to the object (9).

20 Claims, 11 Drawing Sheets

ELECTRONIC COMPONENT MOUNTING APPARATUS

TECHNICAL FIELD

The present invention relates to an electronic component mounting apparatus for recognizing a mark provided at a specific location on a printed circuit board, and mounting an electronic component on the printed circuit board.

BACKGROUND ART

As commonly known, an electronic component mounting apparatus for mounting electronic components on a printed circuit board recognizes a mark on the printed circuit board and positions the electronic or other component to be mounted during the mounting operation using, for example, a CCD camera or sensors. An illumination device is used, during object recognition, to emit light onto or near the object and thus illuminate the object.

Figure 12:
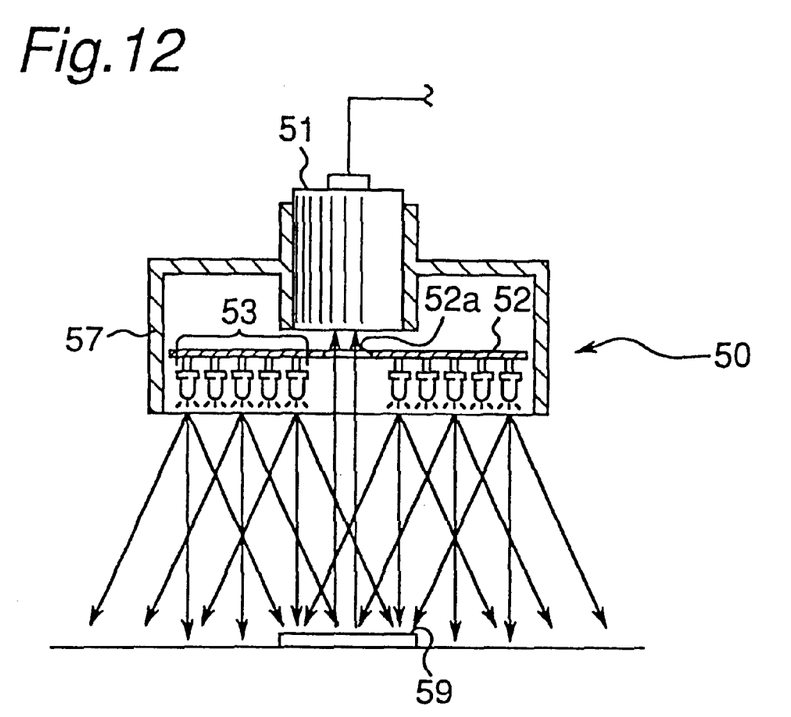
FIG. 12 is a section view showing the gathering of light on an object during illumination by a conventional illumination device.

An example of a conventional illumination device is shown in FIG. 12. This illumination device 50 has a CCD camera 51 for recognizing an object 59, and the camera 51 is located at the top center of a case 57. An illumination source unit 52 comprising a plurality of light sources 53 (such as light bulbs or LEDs) is arranged below the CCD camera 51. An aperture 52a is formed in the middle of the illumination source unit 52 to capture light reflected from the object.

With an illumination device 50 according to this conventional arrangement, a portion of the light emitted from each of the light sources 53 in the illumination source unit 52 irradiates the object 59, and the light reflected therefrom passes through the aperture 52a and is captured by the CCD camera 51, as indicated by solid arrows in FIG. 12. It should be noted that with this conventional illumination device 50, all of the light sources 53 in the illumination source unit 52 are turned on in use, so that light is uniformly emitted to the object 59.

Recently, various materials each having a particular surface condition are used as the electronic components and as a mark on the printed circuit board, and various surface treatments are performed. Thus, various improvements have also been made to the illumination device so that it is possible to satisfactorily recognize a variety of objects having various surface conditions.

Figure 13:
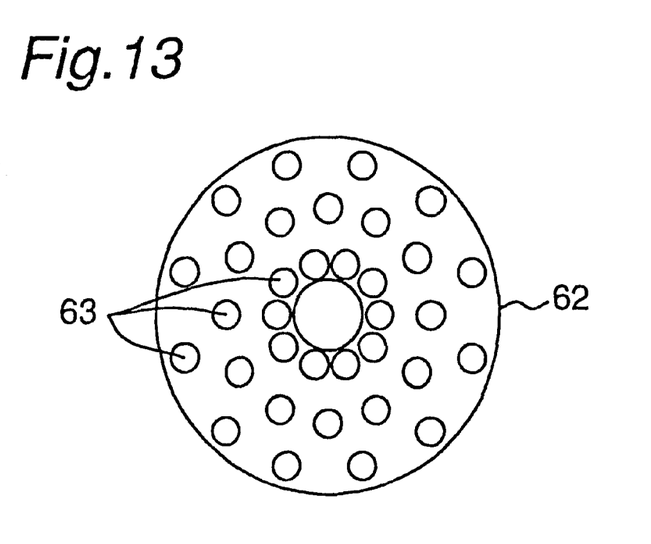
FIG. 13 is a plan view of an illumination source unit in a further conventional illumination device.

FIG. 13 shows an illumination source unit 62 in an illumination device according to another conventional arrangement. In this illumination source unit 62, numerous light sources 63 are arranged in a plurality of circles having different diameters (that is, concentrically) such that light sources 63 on the same circle form a light source group, and the quantity of light can be adjusted for each light source group. The quantity of light from the sources 63 in each circle is then adjusted according to the surface condition of the object so that the optimum illumination is provided for object recognition.

Even with an illumination device unit having an illumination source unit 62 as described above, however, if the quantity of light from the sources 63 chosen to be turned on is not sufficient, the illumination required for object recognition cannot be achieved, and the recognition rate may drop or detection errors may occur.

Furthermore, because all of the light sources 63 are arranged on the same plane and oriented in the same direction, the illumination angle of the light becomes dependent on the directivity of the light sources 63. Thus, it is difficult to achieve sufficient brightness at a desired illumination angle. Because of this, it is conceivable to increase brightness, for example, by increasing the number of light sources 63 or by increasing the quantity of light from each light source 63. This, however, can cause such problems as an increase in current consumption, a drop in the stability of the brightness as a result of heat emitted by the light source, and shortened service life in the light sources 63.

Both the light incidence side and emission side of the light path adjusting member may be divided into a plurality of subareas, each having a different index of refraction, and both light-transmitting surfaces of each subarea are segments of a convex curved surface. The light-emitting surface of each subarea may be formed in the shape of a ground glass surface.

Further, the illumination source unit may comprise a plurality of light sources directed toward each subarea of the light path adjusting member, and the light sources can be selectively turned on. Each of the light sources may emit light with a color complementary to a color of the printed circuit board or mark thereon, and may comprise a plurality of light-emitting elements of different colors.

A first advantage of the electronic component mounting apparatus according to the invention is that the mounting apparatus can emit appropriate illuminating light toward an object, and thus accomplish object recognition and mounting operations satisfactorily, because the apparatus comprises, as a device for recognizing a-mark on a printed circuit board, an illumination device with a light path adjusting member disposed between an illumination source unit for illuminating an object and the object to which the illumination is to be emitted. At least the light incidence side or irradiation side of the light path adjusting member is divided into a plurality of subareas each having a different index of refraction, and thus collects the emitted light on a specific area containing the object by emitting light incident from the illumination source unit at different indexes of refraction.

Further, a second advantage of the electronic component mounting apparatus according to the invention is that illumination light passing each subarea can be gathered toward the center of the irradiated light. This is achieved because at least the light incidence side or irradiation side of the light path adjusting member is divided into a plurality of subareas forming concentric circles, and the index of refraction on the irradiation side of each subarea band decreases as it is closer to the center.

Moreover, a third advantage of the electronic component mounting apparatus according to the invention is that light from the illumination source unit is refracted and directed toward the object at all points on each light-transmitting surface. Therefore, the light can be precisely gathered on the object because the light-transmitting surface of the plural subareas in the light path adjusting member is a segment of a curved surface, the curvature of which differs in each subarea.

Yet further, a fourth advantage of the electronic component mounting apparatus according to the invention is that a significant light-gathering effect can be achieved using refraction on both sides of the light path adjusting member. This is achieved because both the light incidence side and the irradiation side of the light path adjusting member are divided into a plurality of subareas, each having a different index of refraction, and both light-transmitting surfaces of each subarea are segments of a convex curved surface.

Yet further, a fifth advantage of the electronic component mounting apparatus according to the invention is that light from the illumination source unit can be diffused and emitted to a specific area including an object, without dropping the light gathering effect of each light-transmitting surface with a specific index of refractions. This is achieved because the light-emitting surface of each subarea is formed in the shape of a ground glass surface.

Yet further, a sixth advantage of the electronic component mounting apparatus according to the invention is that when the light sources of the illumination source unit are selectively turned on so as to emphasize the contrast between a mark and the printed circuit board forming the background thereto, an even clearer image can be obtained. Furthermore, the accuracy of mark recognition by the apparatus can be improved, because the illumination source unit comprises a plurality of light sources directed toward each subarea of the light path adjusting member, and the light sources can be selectively turned on.

Yet further, a seventh advantage of the electronic component mounting apparatus according to the invention is that the overall illumination source unit can emit the illumination light adjusted to a color complementary to the color of the printed circuit board or mark on the printed circuit board. Therefore, a contrast between the mark and the printed circuit board can thereby be enhanced, an even clearer image can be obtained, and the accuracy of mark recognition by the apparatus can be improved, because each light source can emit light of a color complementary to a color of the printed circuit board or mark thereon.

Yet further, an eighth advantage of the electronic component mounting apparatus according to the invention is that each light source can internally produce a color complementary to the color of the printed circuit board or mark. Illumination of this complementary color can be directly emitted from each light source,.and illumination light free of color irregularities can be emitted, because each light source comprises a plurality of light-emitting elements of different colors. As a result, contrast between a mark and printed circuit board can be reliably enhanced suitably according to the surface condition of any printed circuit board or mark. Furthermore, it is not necessary to provide separate light sources for each color, for example, red, green, and blue, in an illumination source unit comprising such light sources. The number of light sources can therefore be reduced, and reduction in the size and weight of the illumination source unit can thereby be promoted.

DETAILED DESCRIPTION OF THE INVENTION

A preferred embodiment of the present invention is described in detail below with reference to the accompanying figures.

Figure 1:
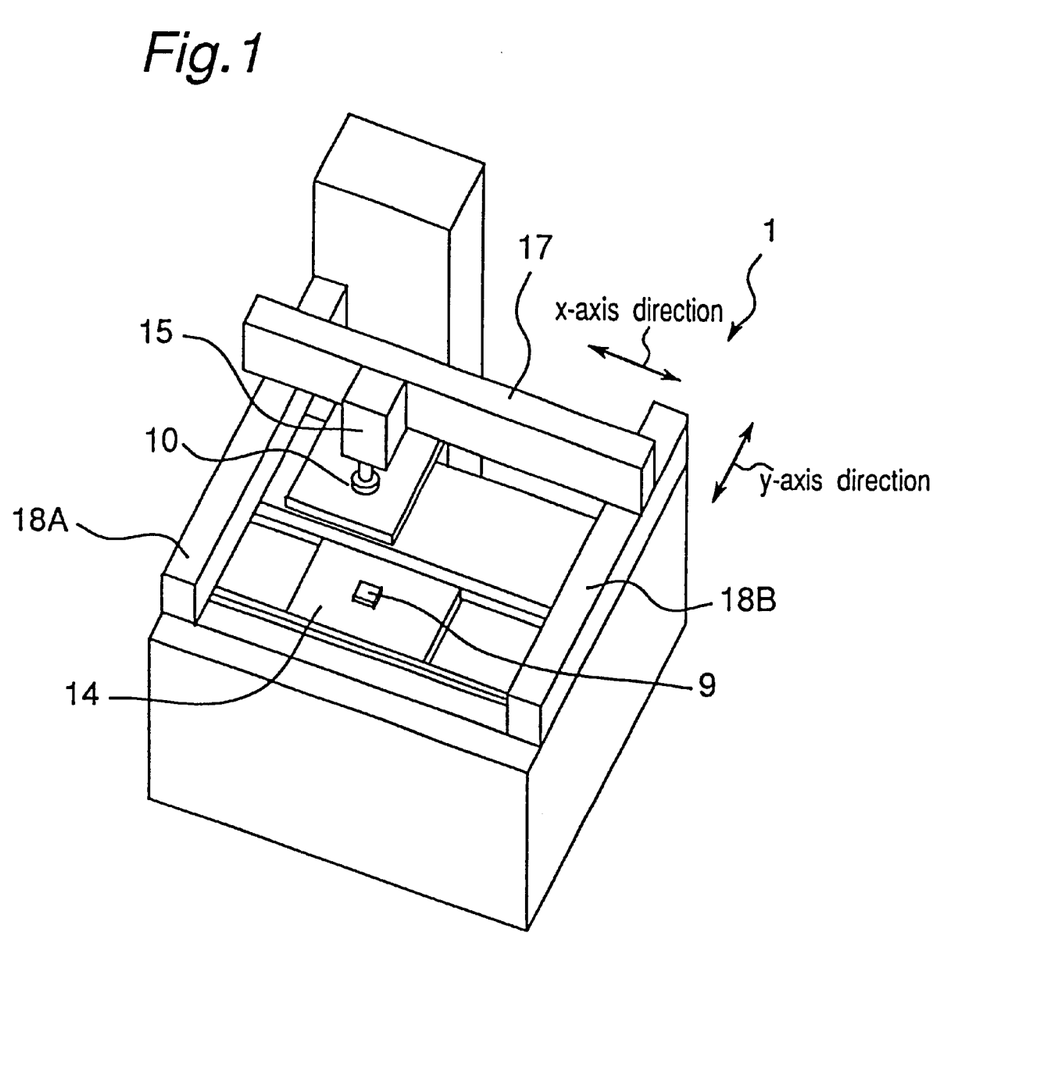
FIG. 1 is a schematic oblique view showing the overall configuration of a mounting apparatus according to a preferred embodiment of the present invention.

FIG. 1 is a schematic oblique view of the overall configuration of an electronic component mounting apparatus 1 according to a preferred embodiment of the present invention. This electronic component mounting apparatus 1 recognizes, for example, a mark 9 for positioning provided at a specific position on a printed circuit board 14, and mounts an electronic component on the printed circuit board 14. The mounting apparatus 1 comprises an illumination device 10 for illuminating the mark 9 during a mark recognition operation. It should be noted that the surface condition of the object to be recognized (that is, the mark 9), may be formed in various manners. For example, the surface may be coated with solder (a so-called solder mark).

This illumination device 10 is included in a head unit together with a CCD camera (see FIG. 2) for imaging the mark 9. This head unit 15 is controlled by an x-axis drive unit 17, and y-axis drive units 18A and 18B for moving the x-axis drive unit 17 in the y-axis direction, which are part of a two-axis (x-y) robot. The illumination device 10 can thus move freely above the printed circuit board 14 as the head unit 15 is driven.

Figure 2:
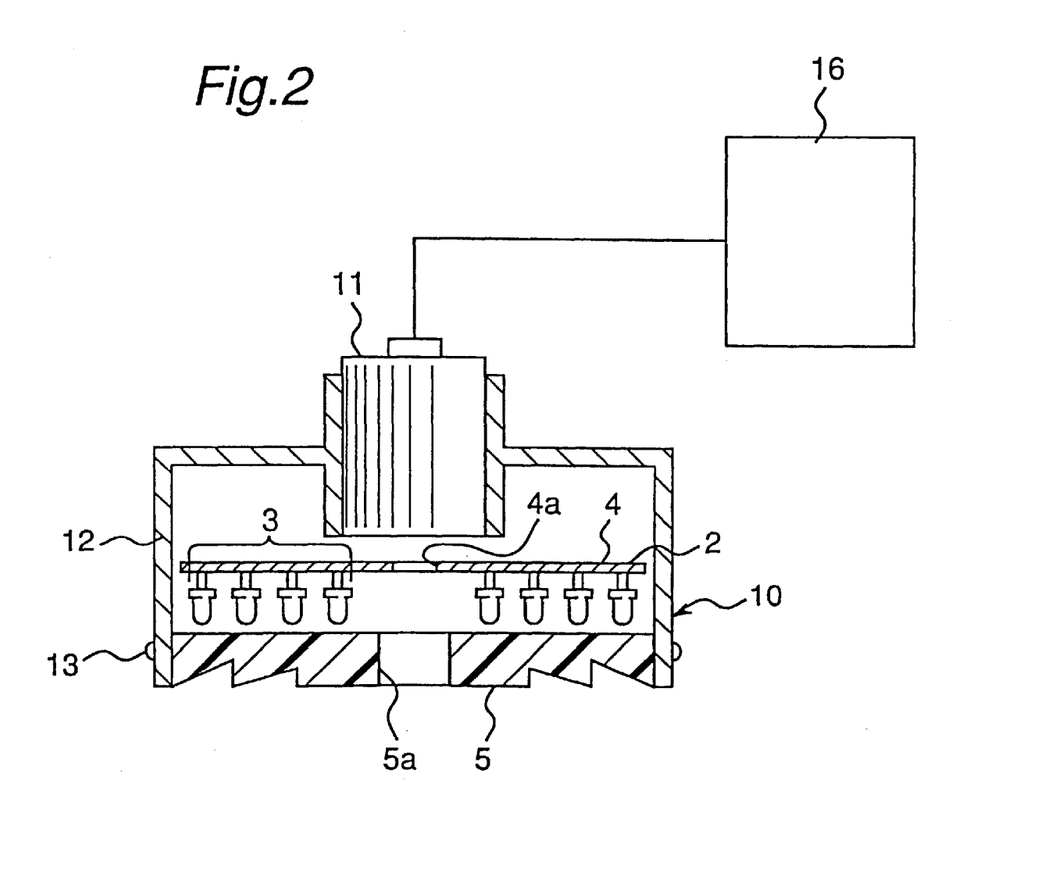
FIG. 2 is a vertical descriptive section view of the illumination device provided in the above mounting apparatus.
Figure 3:
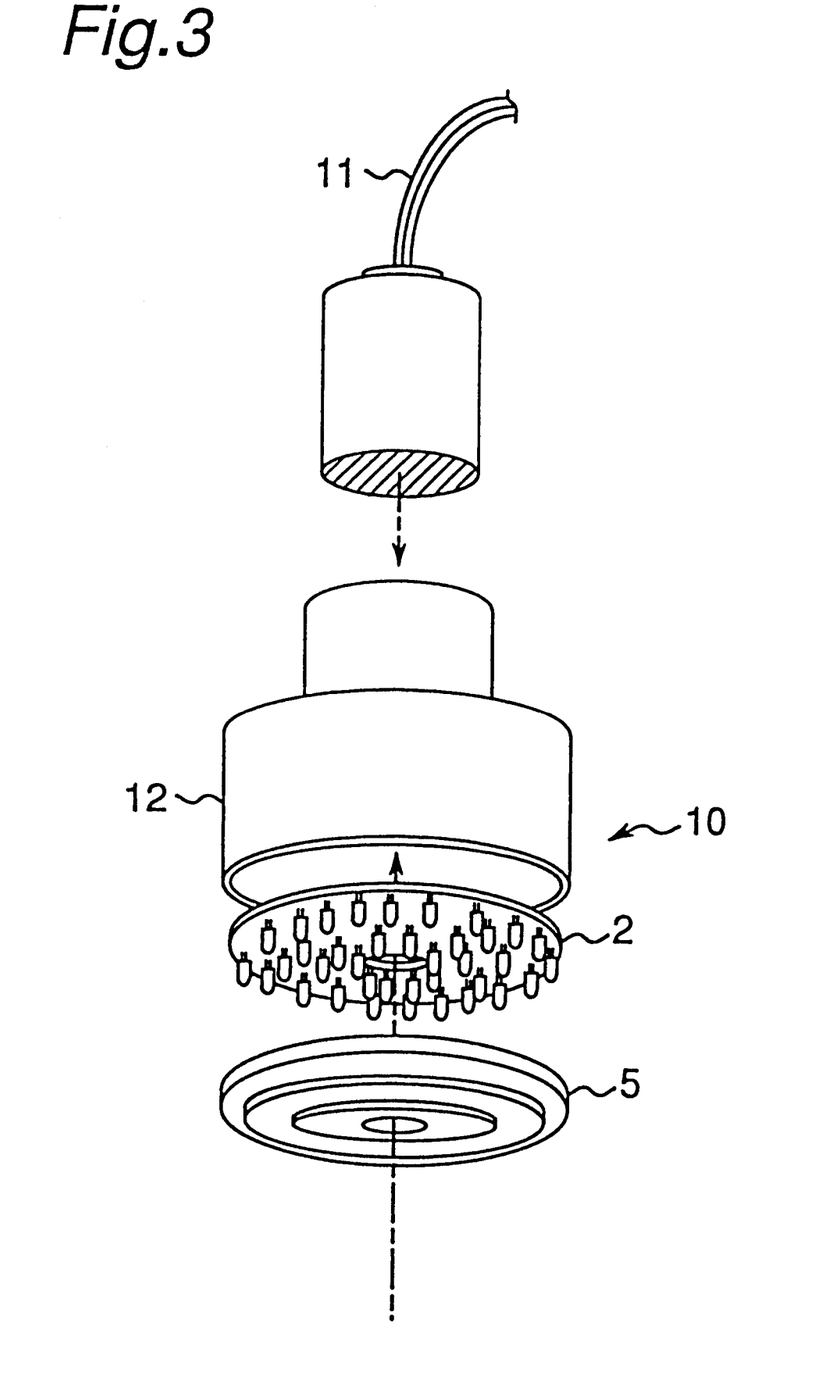
FIG. 3 is an oblique view of the illumination device.

FIG. 2 and FIG. 3 are a vertical cross section and a partially exploded oblique view, respectively, showing the overall configuration of the illumination device 10. With this illumination device 10, a CCD camera 11 for object recognition is provided at the top center of a cylindrical case 12. Below the CCD camera 11, an illumination source unit 2 is disposed with a plurality of light sources 3 on a base plate 4. Opposite the illumination source unit 2 and on the emission side thereof, a light path adjustable plate (light path adjusting member) 5 for adjusting the path of light emitted from the light sources 3 is affixed at the lower part of the case 12 using bolt 13. In this preferred embodiment, the light path adjustable plate 5 is mounted near to the illumination source unit 2 so that light from the light sources 3 can be efficiently picked up. Apertures 4a and 5a for passing therethrough light reflected from a mark (not shown in the FIGS.), which is provided on the printed circuit board as the object to be illuminated by the illumination light during the mounting operation, are formed in the light path adjustable plate 5 and the base plate 4 of the illumination source unit 2. It should be noted that some of the light sources 3 are omitted in FIG. 3 to avoid making the figure too complicated.

With an illumination device 10 thus comprised, a portion of the light from each of the light sources 3 in the illumination source unit 2 irradiates the printed circuit board, and the reflected light passes through the apertures 4a and 5a and is captured by the CCD camera 11. This CCD camera 11 is connected to an image recognition apparatus 16. Reflected light from the object captured by the CCD camera 11 is passed to the image recognition apparatus 16 as an electrical signal, and is recognized as an image as the result of a specific image recognition process.

Figure 4:
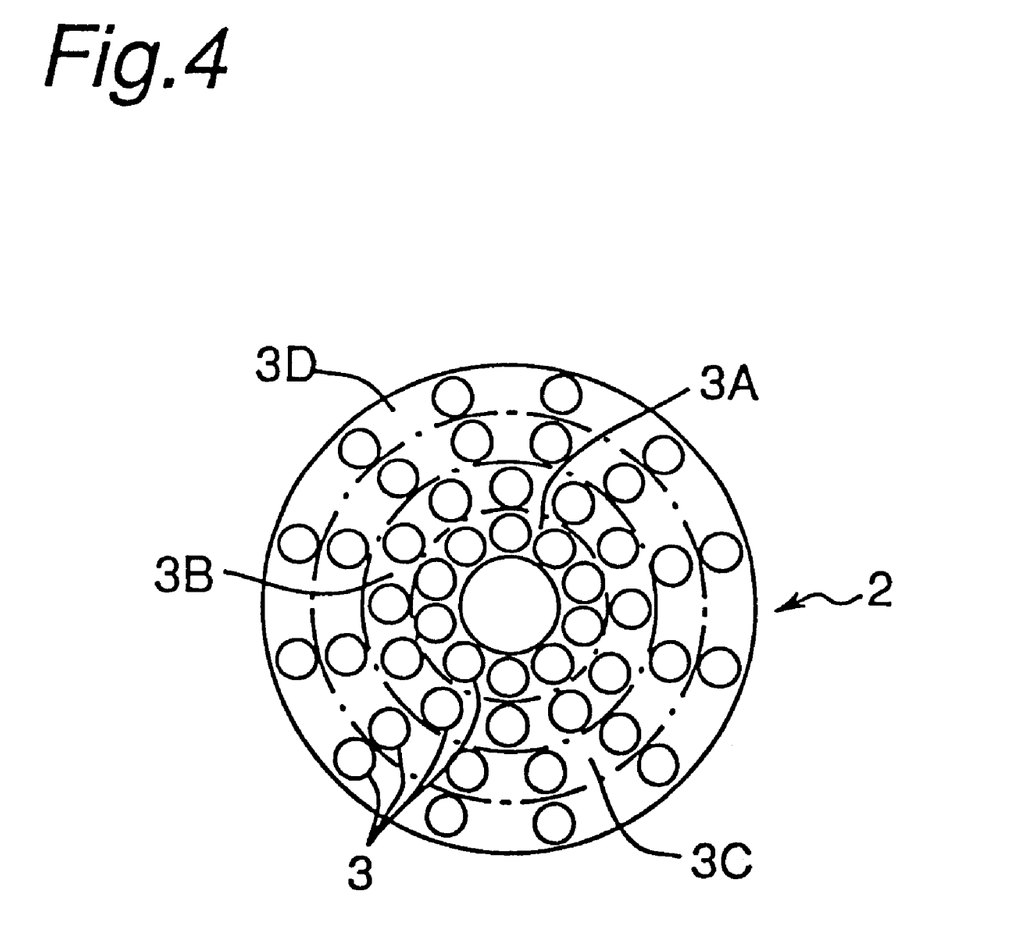
FIG. 4 is a plan view of the illumination source unit in the illumination device.

An arrangement of a plurality of the light sources 3 in the illumination source unit 2 is shown in FIG. 4. In this preferred embodiment, for example, white LEDs can be used as the light sources 3. As will be known from the figure, these light sources 3 are arranged on a circular base plate 4 in a plurality of circles with different diameters (that is, in concentric circles), thus forming four light source groups 3A, 3B, 3C, and 3D. The light source group 3A of the inner-most circle is disposed around the aperture 4a in the center of the base plate 4. The light source group 3D of the outer-most circle is disposed along the outside perimeter of the base plate 4. The light sources 3 comprising these light source groups 3A to 3D are disposed perpendicularly to the base plate 4 and directed toward the light path adjustable plate 5 mounted below the illumination source unit 2.

It should be noted that the light sources 3 are arranged in concentric circles in this illumination source unit 2 so that illumination light with uniform illuminance is emitted in all directions with respect to the optical axis of the CCD camera 11. However, any arrangement can be used insofar as illumination of uniform illuminance can be obtained.

Figure 5A:
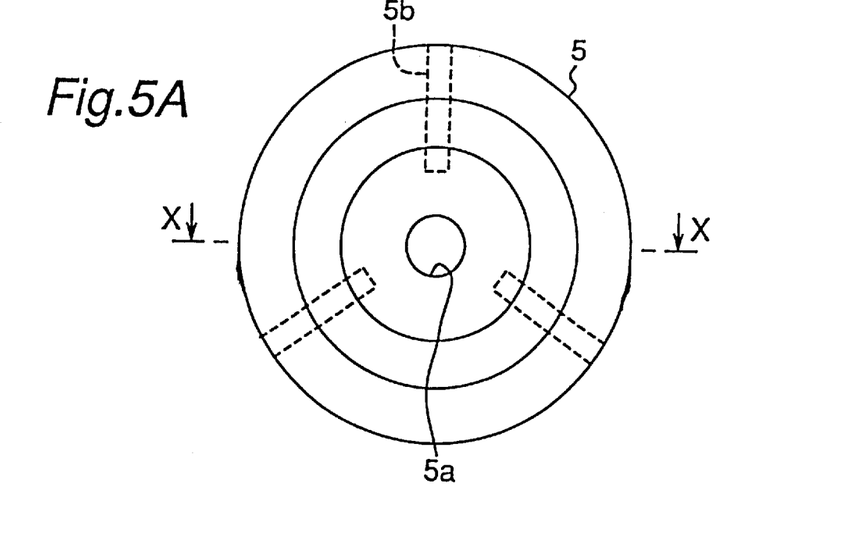
FIG. 5A is a plan view of the light path adjustable member in the illumination device.
Figure 5B:
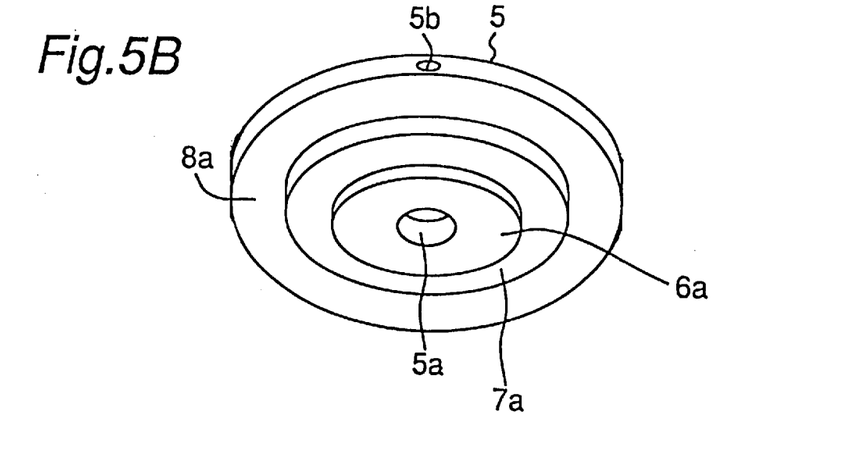
FIG. 5B is an oblique view of the light path adjusting member.
Figure 5C:
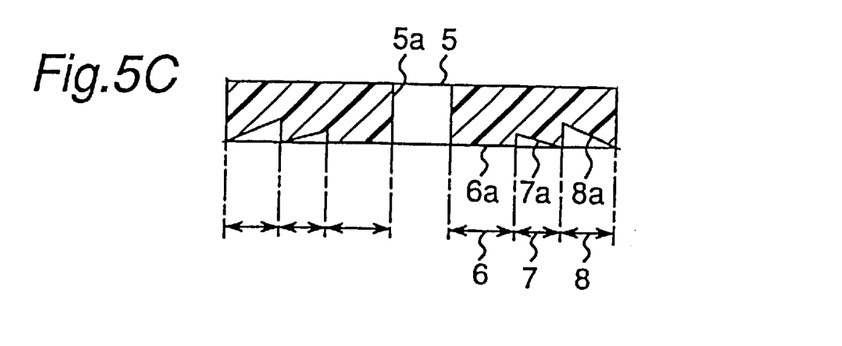
FIG. 5C is a section view through line X—X in FIG. 5A.

A light path adjustable plate 5 as used in this preferred embodiment is shown in FIG. 5A to FIG. 5C. FIG. 5A to FIG. 5C are, respectively, a plan view, an oblique view, and a section view of the light path adjustable plate 5. This light path adjustable plate 5 is formed in a disk shape from a transparent acrylic resin. The emission side of the light path adjustable plate 5 is divided into three belt-shaped (annular) subareas (sub-sections) 6, 7, and 8 forming concentric circles, and a light-transmitting surface 6a, 7a, and 8a, each forming a different angle with respect to the planar direction of the light path adjustable plate 5, is formed in each of these belt-shaped subareas 6, 7, and 8. A radial opening 5b is also provided in the light path adjustable plate 5 from the circumferential surface thereof toward the center of the light path adjustable plate 5 for accepting a bolt 13 (see FIG. 2) when the light path adjustable plate 5 is mounted to the case 12.

The light-transmitting surface 6a of the belt-shaped subarea 6 at the inner-most location on the emission side of the light path adjustable plate 5 is a surface substantially parallel to the planar direction of the light path adjustable plate 5, while the light-transmitting surfaces 7a and 8a of the belt-shaped subareas 7 and 8 positioned on the outside of the belt-shaped subarea 6 are inclined at a specific angle to the planar direction of this light path adjustable plate 5. In this preferred embodiment, the angle of inclination of the light-transmitting surface 7a in the belt-shaped subarea 7 is smaller than the angle of inclination of the light-transmitting surface 8a in the outside belt-shaped subarea 8.

It should be noted that in this preferred embodiment, the maximum depth and maximum width of the belt-shaped subareas 7 and 8 (not including the belt-shaped subarea 6 at the inner-most location) are set to 1 mm and approximately 3 mm, respectively. Furthermore, while a transparent acrylic resin is used for the light path adjustable plate 5, the invention shall not be so limited, and a light path adjustable plate made, for example, from a transparent or semi-transparent glass or plastic can be alternatively used.

The light-gathering action of the light path adjustable plate 5 in the above-noted illumination device 10 is described below with reference to FIG. 6.

Figure 6:
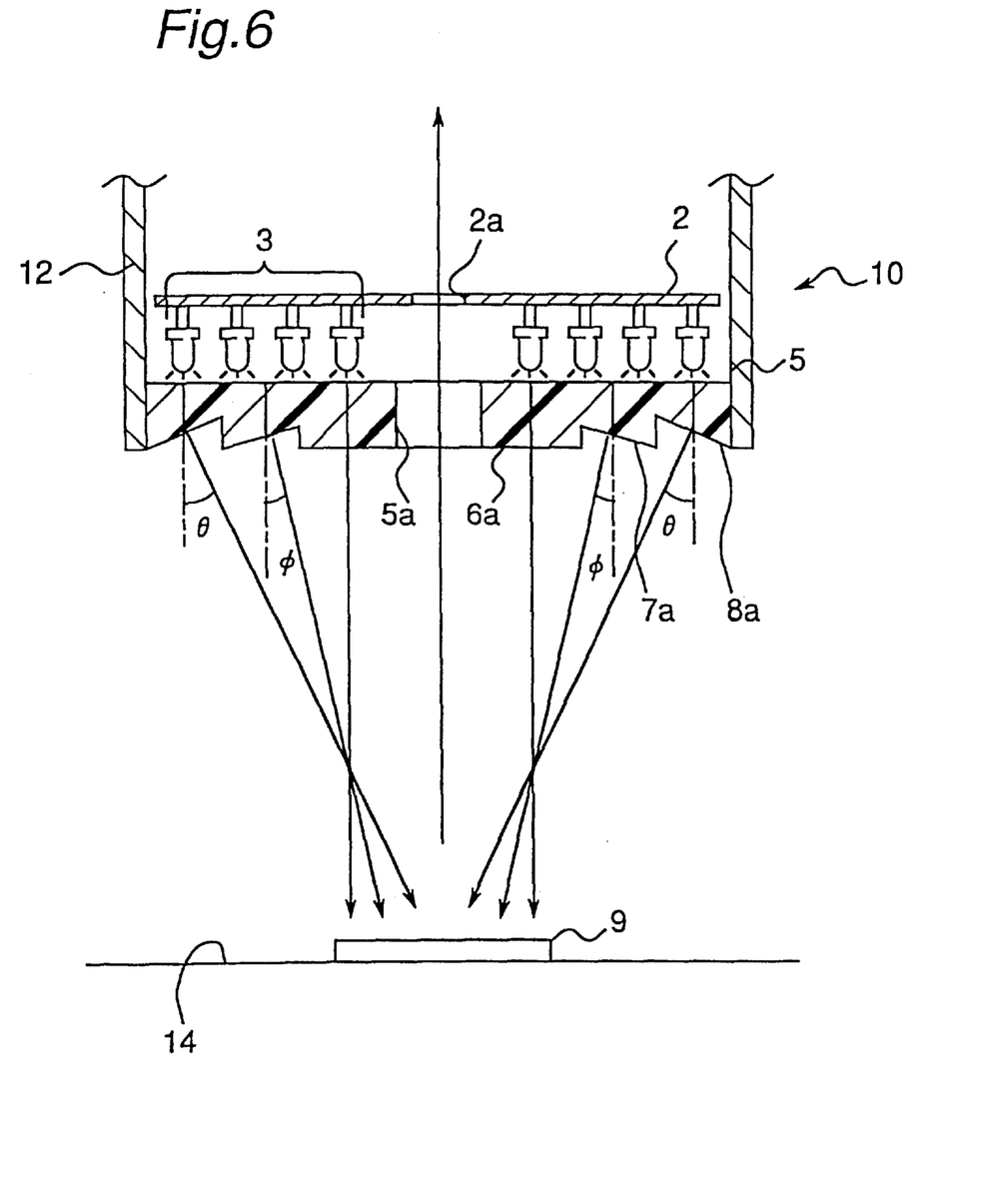
FIG. 6 is a section view showing the gathering of light on an object during illumination by the illumination device.

As shown in FIG. 6, when all of the light sources 3 in the illumination source unit 2 are turned on, light incident from right above subarea 6C at the outer-most location of the light path adjustable plate 5 is refracted at an angle by light-transmitting surface 6c, as indicated by the solid arrows with this illumination device 10. The light incident from right above subarea 6B is refracted at an angle by light-transmitting surface 6b. As described above, because the angle of inclination of light-transmitting surface 6b is smaller than that of light-transmitting surface 6c to the outside thereof in this light path adjustable plate 5, the angle of refraction of the light-transmitting surface 6b is smaller than the angle of refraction of light-transmitting surface 6c.

Furthermore, light incident from right above subarea 6A at the inner-most location of the light path adjustable plate 5 passes the light path adjustable plate 5 without being refracted by the light-transmitting surface 6a (that is, the angle of refraction is 0°).

As a result, light from the illumination source unit 2 that has passed through the light path adjustable plate 5 is concentrated in a specific area on the surface opposite the illumination device 10. That is, by transmitting the light from the illumination source unit 2 through the light path adjustable plate 5, this illumination device 10 can illuminate the printed circuit board 14 and the mark 9 thereon with an appropriate amount of light when positioned opposite the illumination device 10 on the optical axis of the CCD camera 11 (see FIG. 2). In addition, because the light path adjustable plate 5 is arranged near (adjacent to) the illumination source unit 2 in this preferred embodiment, light from light sources 3, which provide a specific amount of light, can be efficiently concentrated on the mark 9.

It is therefore possible, with an illumination device 10 according to this preferred embodiment of the invention, to expose a mark 9 on the printed circuit board 14 with an amount of light suitable for object recognition without increasing the number of light sources or the output of each light source, and without requiring a complicated construction for adjusting the path of the illumination light.

Figure 7A:
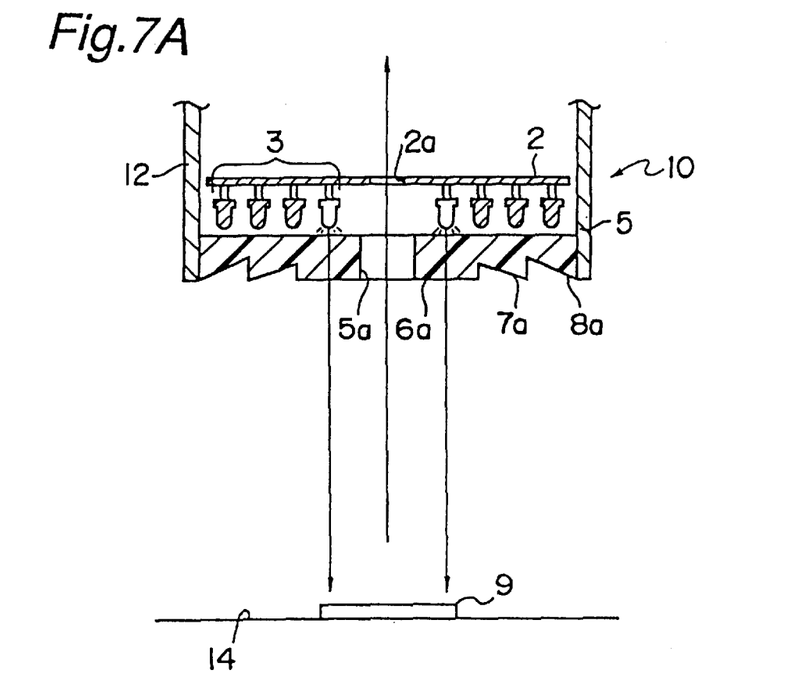
FIG. 7A is a section view of an illumination source unit in which light sources are selectively turned on according to the mirror surface condition of a mark.
Figure 7B:
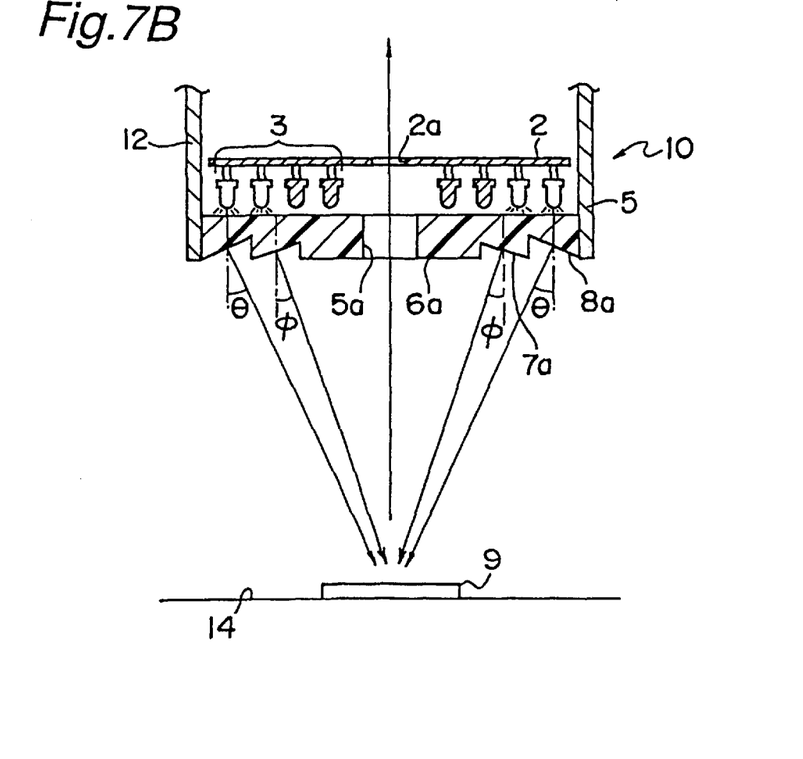
FIG. 7B is a section view of an illumination source unit in which light sources are selectively turned on according to the mirror surface condition of a printed circuit board.

It should also be noted that a specific illumination control means (not shown in the FIGS.) can be provided for this illumination device 10 to adjust the output of the light sources 3 or to turn on only part of the light sources 3 in the illumination source unit 2 opposing the light path adjustable plate 5 according to the surface condition of the printed circuit board 14 and the mark 9 thereon. FIG. 7A and FIG. 7B are descriptive section views of an illumination device 10 in which part of the light sources 3 are selectively turned on according to different surface conditions.

If the surface of the mark 9 is a mirror surface, such as if a mark 9 on a ceramic printed circuit board 14 is coated with solder, when light is emitted from a direction at an obtuse angle to the optical axis of the CCD camera 11 (see FIG. 2), the illumination light will be totally reflected with substantially no light entering the CCD camera 11. In this case, therefore, only the light sources 3 belonging to the light source group 3A (see FIG. 4) at the inner-most circumference are turned on so that the illumination light is totally reflected at the surface of the mark 9 and picked up by the CCD camera 11 as shown in FIG. 7A.

Furthermore, if the surface of the printed circuit board 14 is a near-mirror surface, such as if a copper mark is formed on a printed circuit board made from glass epoxy, only the light sources 3 belonging to the light source groups 3C and 3D (see FIG. 4) at the outer circumference are turned on as shown in FIG. 7B. In this case, the light incident to the printed circuit board 14 is totally reflected, and substantially no light enters the CCD camera 11. On the other hand, light incident to the mark 9 is randomly reflected, and part of the light enters the CCD camera 11. As a result, the mark 9 is seen brighter than the printed circuit board 14 in the background.

By thus selectively turning on the light sources 3 of the illumination source unit 2 to emphasize the contrast between a mark 9 and the background printed circuit board 14 according to the surface condition of the printed circuit board 14 and mark formed thereon, an even clearer image can be obtained by the CCD camera 11, and the accuracy of the mark 9 recognition by the apparatus can be improved.

Yet further, the emission side of the light path adjustable plate 5 is divided into three subareas (sub-sections) 6, 7, and 8 in this preferred embodiment, but the present invention is not so limited. For example, the emission side of the light path adjustable plate 5 can be divided into only two, or more than three, subareas. In particular, when divided into more than three subareas, light from the illumination source unit can be even more efficiently concentrated on the object, such as the printed circuit board and the mark, by setting a different angle of refraction for the light-transmitting surface of each subarea so that light from the illumination source unit is refracted at a different angle of refraction at each light-transmitting surface. As a result, appropriate illumination light can be emitted for object recognition.

Figure 8:
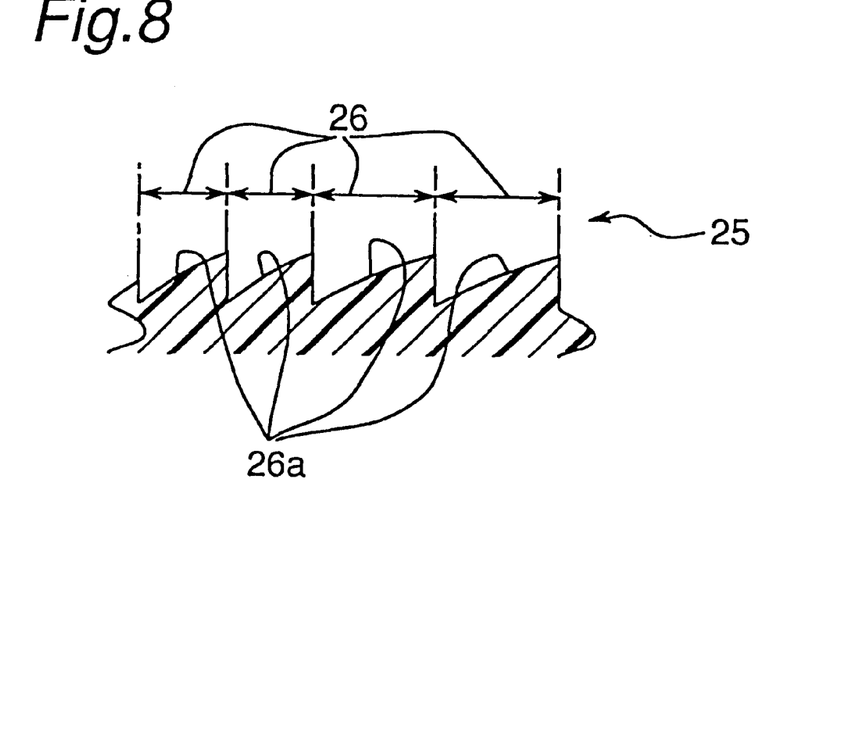
FIG. 8 is a partial section view of a light path adjusting member comprising, in each subarea, a curved light-transmitting surface.

An alteration of the light path adjustable plate is shown in FIG. 8. This light path adjustable plate 25 comprises a plurality of subareas (sub-sections) 26 formed as concentric circles. The, light-transmitting surface 26a of each subarea 26 is a curved surface with the curvature thereof differing in each subarea 26. The refractive index of each subarea 26 decreases the closer it is to the center. When a light path adjustable plate 25 thus comprised is used, light from the illumination source unit is refracted at each point of each light-transmitting surface 26a so that it is directed toward the object, such as the printed circuit board and the mark. As a result, light from the illumination source unit can be accurately concentrated on the printed circuit board and the mark.

Figure 9:
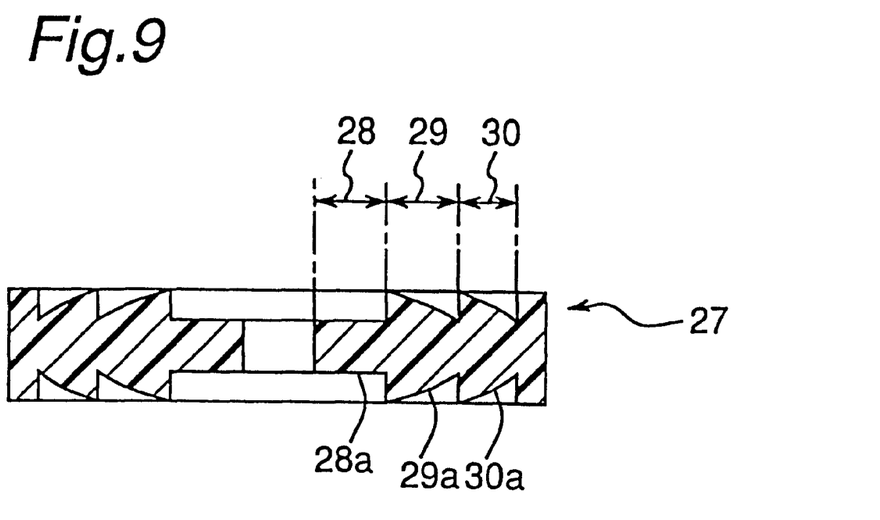
FIG. 9 is a section view of a light path adjusting member divided on both sides thereof into a plurality of subareas.

A further alternative version of the light path adjustable plate is shown in FIG. 9. With this light path adjustable plate 27, both the light incidence and emission sides of the light path adjustable plate 27 are divided into belt-shaped (annular) subareas 28, 29, and 30 forming concentric circles. Each of these subareas has a light-transmitting surface 28a, 29a, and 30a, each having a different curvature. In particular, light-transmitting surfaces 29a and 30a have a convex curve. The refractive index of each subarea 28, 29, and 30 decreases the closer it is to the center. The light gathering effect of this light path adjustable plate 27 is greater than that of a light path adjustable plate having subareas formed on only one side of the plate, and can more efficiently concentrate light on the printed circuit board and the mark.

Though not specifically shown in the figure, the light-transmitting surfaces of this light path adjustable plate can have a pear-skin surface (that is, a rough ground glass surface). In this case, light from the illumination source unit can be emitted to a specific area including the object while diffusing the light to the extent that the light gathering effect of each light-transmitting surface having a specific refractive index is maintained.

Figure 10:
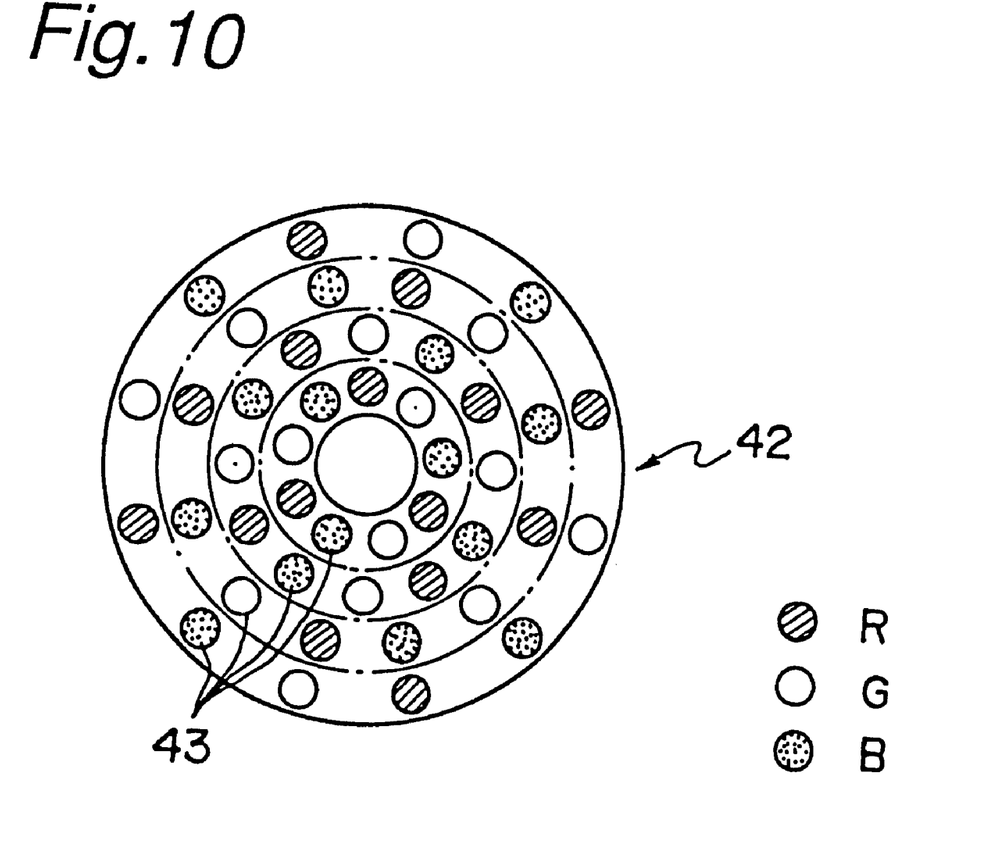
FIG. 10 is a plan view of an illumination source unit according to an alternative embodiment of the present invention.

It should be further noted that while the above-noted preferred embodiments are described using white LEDs as the light sources 3 of the illumination source unit 2, the present invention is not so limited. For example, a light source such as an LED that emits any of the colors red, green, and blue can be used. FIG. 10 shows an illumination source unit 42 comprising such a light source.

In this illumination source unit 42, the light sources 43 are arranged in concentric circles with each light source 43 containing LEDs capable of emitting red, green, or blue. The illumination source unit 42 can produce light with the color composed of RGB with brightness and chroma adjusted by controlling the current supplied to each light source 43. As a result, the illumination source unit 42 can emit light in a plurality of colors.

For example, when the recognition mark is on a green printed circuit board, it is therefore possible using an illumination source unit 42 thus comprised to emit "red" light (that is, light with a color complementary to green) by turning on only the red light sources. Thus, the printed circuit board is darkened, which forms a dark background of the mark. Insofar as the mark is not greenish, the "red" light illuminating the mark will be picked up by the CCD camera, and an even clearer image with emphasized contrast between the printed circuit board and mark can be obtained.

Furthermore, if the mark on the printed circuit board is red, for example, it is also possible in this embodiment to turn on the green and blue light sources, control the current supply to each light source to produce "blue-green" light (that is, light with a color complementary to red), and thus darken the printed circuit board forming the background to the mark.

It is also possible to emphasize the contrast between the printed circuit-board and the mark by forming a color complementary to the color of the mark and thereby darken the mark. For example, if a mark is made with yellow adhesive on a white printed circuit board, it is possible to turn on the red and blue light sources of the illumination source unit 42 and control the current supply to the light sources to form a bluish-violet light (that is, a light with a color complementary to yellow). As a result, the mark is darkened, while the bluish-violet illumination emitted to the printed circuit board is picked up by the CCD camera, resulting in the contrast between the printed circuit board and mark being enhanced.

As thus described, it is possible with an illumination source unit 42 comprising, for example, RGB light sources 43, to produce a color complementary to the color of the printed circuit board or the mark by controlling the current supply to the light sources 43, and thereby enhance the contrast between the printed circuit board and mark. As a result, the CCD camera can capture an even clearer image, and the accuracy of the mark recognition by the apparatus can be improved.

The illumination source unit can further alternatively comprise a light source capable of emitting a plurality of colors, such as a 3-in-1 type LED, as a light source for producing a color complementary to the color of the printed circuit board or mark. This 3-in-1 LED contains an RGB three color LED, and can alone emit light in a plurality of colors by controlling the current for each color to adjust the brightness and chroma.

Figure 11:
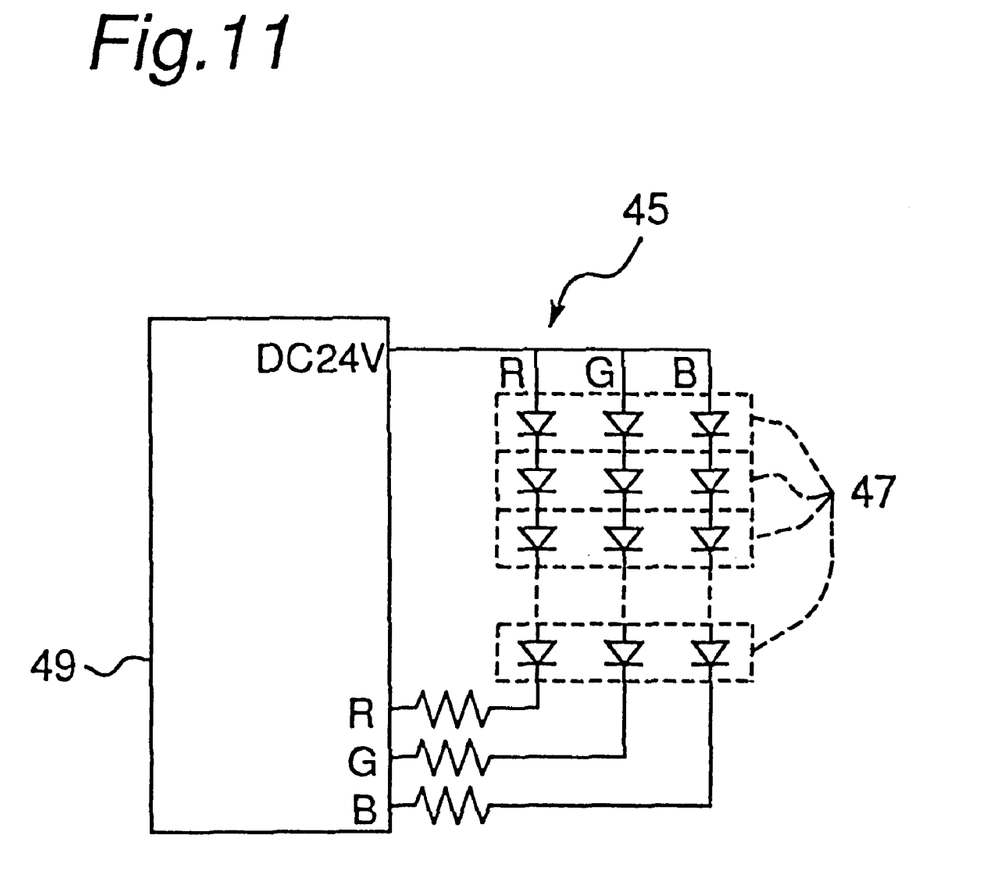
FIG. 11 is a circuit diagram of an illumination circuit according to a further alternative embodiment of the present invention.

FIG. 11 is a circuit diagram showing an exemplary illumination circuit containing such a 3-in-1 LED. The plural 3-in-1 LEDs provided in this illumination circuit 45 are composed of RGB LEDs arranged in a row by color. In this circuit 45, all of the 3-in-1 LEDs are connected in series. The current flow to these 3-in-1 LEDs 47 is controlled for each color of LED by an illumination controller 49 in this illumination circuit 45. With an illumination circuit 45 in which LEDs are connected in series as noted above, power consumption is relatively low.

With an illumination source unit 40 as shown in FIG. 10, each light source 43 emits only one color, red, green, or blue, and different colors of light from the light sources 43 mix on the printed circuit board and the mark to form a complementary color. This can result in color irregularities or a rainbow of colors reflected from the surface of the printed circuit board or the mark, if the surface of the printed circuit board or mark is uneven, for example, because different colors emitted from different angles thus reflect at correspondingly different angles.

With an illumination source unit comprising 3-in-1 LED 47 light sources, each light source can be driven to emit light already adjusted to the color complementary to the color of the printed circuit board or the mark. Illumination with no color irregularities can thus be emitted. As a result, the contrast between the printed circuit board and mark can be reliably emphasized according to the surface condition of the printed circuit board or mark.

What is claimed is:

1. An electronic component mounting apparatus for recognizing a mark provided at a specific location on a printed circuit board, and for mounting an electronic component on the printed circuit board, said mounting apparatus comprising an illumination device including:
    an illumination source unit for emitting light in the direction of an object, said illumination source unit including a plurality of light sources; and
    a light path adjusting member having a light incidence side and an emission side, at least one of said light incidence side and said emission side having a plurality of annular sub-sections arranged to form concentric circles, said annular sub-sections having different indexes of refraction, said light path adjusting member being arranged between said illumination source unit and the object to be illuminated by the light emitted from said illumination source unit so as to direct the light emitted from said illumination source unit and incident on said light path adjusting member onto the object via at least one of said annular sub-sections having a respective one of said indexes of refraction;
    wherein said light sources of said illumination source unit are arranged in a circle having a diameter corresponding to a diameter of one of said annular sub-sections of said light path adjusting member, said light sources being arranged to emit light toward said one of said annular sub-sections of said light path adjusting member.

2. The mounting apparatus of claim 1, wherein said at least one of said light incidence side and said emission side having said plurality of annular sub-sections has a sawtooth-shaped cross section.

3. The mounting apparatus of claim 2, wherein an innermost one of said annular sub-sections has a surface substantially parallel to a plane of said light path adjusting member.

4. The mounting apparatus of claim 2, wherein said annular sub-sections are arranged such that an index of refraction of any one of said annular sub-sections is less than an index of refraction of an adjacent annular sub-section located farther from a center of said light path adjusting member than said one of said annular sub-sections.

5. The mounting apparatus of claim 2, wherein said illumination source unit comprises a plurality of groups of light sources, each of said groups of light sources being arranged in one of a plurality of circles having different diameters, a diameter of each of said circles corresponding to a diameter of a respective one of said annular sub-sections.

6. The mounting apparatus of claim 2, wherein each of a group of said annular sub-sections has a curved surface, said group of said annular sub-sections having curved surfaces with different curvatures.

7. The mounting apparatus of claim 1, wherein an innermost one of said annular sub-sections has a surface substantially parallel to a plane of said light path adjusting member.

8. The mounting apparatus of claim 7, wherein said annular sub-sections are arranged such that an index of refraction of any one of said annular sub-sections is less than an index of refraction of an adjacent annular sub-section located farther from a center of said light path adjusting member than said one of said annular sub-sections.

9. The mounting apparatus of claim 7, wherein said illumination source unit comprises a plurality of groups of light sources, each of said groups of light sources being arranged in one of a plurality of circles having different diameters, a diameter of each of said circles corresponding to a diameter of a respective one of said annular sub-sections.

10. The mounting apparatus of claim 7, wherein each of a group of said annular sub-sections has a curved surface, said group of said annular sub-sections having curved surfaces with different curvatures.

11. The mounting apparatus of claim 1, wherein said annular sub-sections are arranged such that an index of refraction of any one of said annular sub-sections is less than an index of refraction of an adjacent annular sub-section located farther from a center of said light path adjusting member than said one of said annular sub-sections.

12. The mounting apparatus of claim 11, wherein said illumination source unit comprises a plurality of groups of light sources, each of said groups of light sources being arranged in one of a plurality of circles having different diameters, a diameter of each of said circles corresponding to a diameter of a respective one of said annular sub-sections.

13. The mounting apparatus of claim 11, wherein each of a group of said annular sub-sections has a curved surface, said group of said annular sub-sections having curved surfaces with different curvatures.

14. The mounting apparatus of claim 1, wherein said illumination source unit comprises a plurality of groups of light sources, each of said groups of light sources being arranged in one of a plurality of circles having different diameters, a diameter of each of said circles corresponding to a diameter of a respective one of said annular sub-sections.

15. The mounting apparatus of claim 1, wherein each of a group of said annular sub-sections has a curved surface, said group of said annular sub-sections having curved surfaces with different curvatures.

16. The mounting apparatus of claim 15, wherein both said light incidence side of said light path adjusting member and said emission side of said light path adjusting member have a plurality of said annular sub-sections arranged to form concentric circles, said annular sub-sections on each side of said light path adjusting member having different indexes of refraction, each of a group of said annular sub-sections on each side of said light path adjusting member having a convex curved surface.

17. The mounting apparatus of claim 1, wherein each of said annular sub-sections has a ground glass-shaped light emitting surface.

18. The mounting apparatus of claim 1, wherein said light sources are operable to be selectively illuminated.

19. The mounting apparatus of claim 18, wherein each of said light sources is operable to emit light having a color complementary to a color of at least one of the printed circuit board and the mark on the printed circuit board.

20. The mounting apparatus of claim 19, wherein each of said light sources comprises a plurality of light-emitting elements for emitting different colors.

* * * * *